US011180433B2

(12) United States Patent
Castillo-Welter et al.

(10) Patent No.: US 11,180,433 B2
(45) Date of Patent: Nov. 23, 2021

(54) PROCESS AND PLANT FOR PRODUCING METHANOL

(71) Applicant: L'Air Liquide, Société Anonyme pour l'Etude et l'Exploitation des Procédés Georges Claude, Paris (FR)

(72) Inventors: Frank Castillo-Welter, Friedrichsdorf (DE); Stephane Haag, Frankfurt am Main (DE); Timm Schuhmann, Offenbach (DE); Robert Frind, Dresden (DE)

(73) Assignee: L'Air Liquide, Société Anonyme pour l'Etude et l'Exploitation des Procédés Georges Claude, Paris (FR)

( * ) Notice: Subject to any disclaimer, the term of this patent is extended or adjusted under 35 U.S.C. 154(b) by 0 days.

(21) Appl. No.: 16/881,149

(22) Filed: May 22, 2020

(65) Prior Publication Data

US 2020/0369585 A1 Nov. 26, 2020

(30) Foreign Application Priority Data

May 22, 2019 (EP) .................................... 19020337

(51) Int. Cl.
*C07C 29/152* (2006.01)
*B01J 8/02* (2006.01)

(52) U.S. Cl.
CPC .......... *C07C 29/152* (2013.01); *B01J 8/0278* (2013.01); *B01J 8/0285* (2013.01); *B01J 2208/00256* (2013.01)

(58) Field of Classification Search
CPC ... C07C 29/152; C07C 31/04; C07C 29/1516; C07C 29/151
See application file for complete search history.

(56) References Cited

U.S. PATENT DOCUMENTS

2016/0083319 A1\* 3/2016 Hackel ................. C07C 29/152
29/401.1
2019/0016655 A1\* 1/2019 Yiu ......................... B01J 23/72

FOREIGN PATENT DOCUMENTS

| DE | 101 26 719 | 12/2002 |
|----|------------|---------|
| GB | 2 550 993 | 12/2017 |
| WO | WO 2017 121981 | 7/2017 |

OTHER PUBLICATIONS

European Search Report for corresponding EP 19020337, dated Nov. 4, 2019.

\* cited by examiner

*Primary Examiner* — Jafar F Parsa
(74) *Attorney, Agent, or Firm* — Elwood L. Haynes (57) ABSTRACT

The invention relates to a process and a plant for producing methanol from an input gas including carbon monoxide and hydrogen using a pre-reactor stage and a main reactor stage. Input gas produced at and under elevated pressure is initially introduced into a pre-reactor stage for catalytic conversion into a first methanol-containing product stream. After separation of methanol from the first methanol-containing product stream and discharging from the pre-reactor stage a remaining gas stream is introduced into a main reactor stage as a residual gas stream after compression to reaction pressure for catalytic conversion into a second methanol-containing product stream, After separation from the second methanol-containing product stream methanol is discharged from the main reactor stage. Using an input gas having a carbon monoxide content of 25% to 36% by volume results in large savings in respect of the compressor output required for the production process.

15 Claims, 2 Drawing Sheets

PROCESS AND PLANT FOR PRODUCING METHANOL

CROSS REFERENCE TO RELATED APPLICATIONS

This application claims the benefit of priority under 35 U.S.C. § 119 (a) and (b) to European Patent Application No. 19020337.2, filed May 22, 2019, the entire contents of which are incorporated herein by reference.

BACKGROUND

Field of the Invention

The invention relates to a process for producing methanol from an input gas comprising carbon monoxide (CO) and hydrogen ($H_2$). The invention further relates to a plant for producing methanol from an input gas comprising carbon monoxide (CO) and hydrogen ($H_2$).

Prior Art

Today, methanol is typically produced from synthesis gas, an input gas comprising predominantly carbon monoxide (CO) and hydrogen ($H_2$) and generally also carbon dioxide ($CO_2$). In the modern so-called low-pressure processes pressures between 60 and 120 bar are used in the catalytic conversion of synthesis gas into crude methanol. The reaction is carried out over fixed bed catalysts at moderate temperatures of below 300° C. Employed catalysts include for example materials based on copper/zinc oxide/aluminum oxide.

Synthesis gas from steam reforming is generally produced at pressures between 20 and 40 bar and must initially be compressed via a synthesis gas compressor to the higher pressure (reaction pressure) of at least 60 bar required for methanol synthesis. Known processes operate with large volumes of recirculating gas in a so-called synthesis circuit in which the amount of the recirculated gas is up to five times higher than the supplied fresh gas amount from the synthesis gas production. Alternatively to a synthesis circuit the production of the crude methanol may also be carried out in a multistage reactor system having serially arranged reactors. The number of reactors depends on the per pass conversion achievable per reactor.

The gas compressors required for compression of the synthesis gas are machines which incur high operating costs (OPEX) on account of their high energy consumption and also require high capital expenditure (CAPEX) on account of their size and mode of construction. The gas compressors used for compressing the input gases, for example synthesis gas, inclusive of propulsion technology may account for up to 30% of the costs of all main process equipment. The compressor output required for the compression of gases thus contributes greatly to the total cost of a plant for methanol production since not only the size of the compressors but also the output required to operate these compressors increases with the amount of the gases to be compressed.

The main reactor stage of a methanol synthesis which comprises the synthesis circuit or the multistage reactor system may have a pre-reactor stage connected upstream of it in which a portion of the synthesis gas is converted into methanol before introduction into the main reactor stage. The pre-reactor stage typically comprises a single pre-reactor which the synthesis gas traverses in a single pass and at whose outlet the produced methanol is separated (condensed) before the remaining synthesis gas (residual gas) is sent on to the main reactor stage. The process mode comprising a pre-reactor has the advantage that only the remaining synthesis gas (residual gas) and not the total amount of the synthesis gas need be compressed to the pressure in the main reactor stage by the synthesis gas compressor.

In the pre-reactor the input gas supplied from the synthesis gas production may be converted into methanol without prior compression with a compressor, as described for example in DE 101 26 719 A1. The thus achievable energy savings for the synthesis gas compressor arranged downstream of the pre-reactor are often low since only a small conversion of synthesis gas to methanol is achieved in the pre-reactor stage. This ultimately has the result that despite the use of a pre-reactor which increases the capital and operating costs of the plant the majority of the synthesis gas is to be introduced into the main reactor stage. The costs saved in respect of the synthesis gas compressor arranged downstream of the pre-reactor stage (OPEX and CAPEX) are thus compensated in a negative sense by the use of the pre-reactor.

SUMMARY

It is accordingly an object of the present invention to at least partially overcome the disadvantages of the prior art.

It is a further object of the present invention to provide a process allowing significantly higher energy savings in respect of the gas compressors used for the compression of input gases.

It is a further object of the present invention to provide a process which increases the conversion of input gas, in particular synthesis gas, in the pre-reactor, so that the residual gas amount for subsequent compression is significantly reduced.

It is a further object of the present invention to provide a plant which at least partially solves the abovementioned objects.

The objects of the invention are at least partially achieved by a process for producing methanol from an input gas comprising carbon monoxide (CO) and hydrogen ($H_2$), wherein input gas produced at and under elevated pressure is introduced into a pre-reactor stage as an input gas stream for catalytic conversion into a first methanol-containing product stream and methanol is separated from the first methanol-containing product stream and discharged from the pre-reactor stage and residual gas of the remaining input gas stream is compressed to reaction pressure as a residual gas stream and introduced into a main reactor stage for catalytic conversion into a second methanol-containing product stream and methanol is separated from the second methanol-containing product stream and discharged from the main reactor stage. According to the invention it is provided that the input gas has a carbon monoxide content of 25% to 36% by volume before introduction into the pre-reactor stage.

The input gas preferably has a carbon monoxide content of 27% to 33% by volume, particularly preferably a carbon monoxide content of 28% to 31% by volume and more preferably a carbon monoxide content of 29% to 30% by volume before introduction into the pre-reactor stage.

The input gas is preferably a synthesis gas from coal gasification.

It has now been found that, surprisingly, the energy savings in the gas compressor arranged downstream of the pre-reactor when simultaneously using a pre-reactor are markedly higher for an input gas having a carbon monoxide content according to the invention, for example an input gas from coal gasification, than for an input gas having a relatively low carbon monoxide content. Input gases having a relatively low carbon monoxide content are for example input gases from steam reforming of methane (steam methane reforming—SMR) or a combination of steam reforming and autothermal reforming (so-called combined reforming). Synthesis gases produced on the basis of these technologies regularly have CO contents of markedly below 25% by volume.

Due to the higher CO content in the input gas supplied to the pre-reactor, for example an input gas from coal gasification, both the compressor output (energy consumption of the compressor) and the compressor size of an input gas compressor for compressing the residual gas stream, in particular a synthesis gas compressor, may surprisingly be markedly reduced. This results in significant savings in respect of OPEX and CAPEX for the input gas compressor.

A preferred embodiment of the process according to the invention is characterized in that the input gas has a hydrogen content of 66% to 72% by volume before introduction into the pre-reactor stage.

It is particularly preferable when the input gas has a hydrogen content of 67% to 70% by volume and more preferably a hydrogen content of 68% to 69% by volume before introduction into the pre-reactor stage.

Studies have shown that in combination with the inventive carbon monoxide contents in the input gas particularly high yields of methanol in the pre-reactor are achieved, thus resulting in further savings in respect of the input gas compressor.

A preferred embodiment of the process according to the invention is characterized in that the input gas has a carbon dioxide content ($CO_2$ content) of not more than 5% by volume before introduction into the pre-reactor stage.

It is preferable when the input gas has a carbon dioxide content of 2% to 4% by volume, particularly preferably of 2.5% to 3.5% by volume, before introduction into the pre-reactor stage.

Studies have shown that in combination with the inventive carbon monoxide contents and optionally hydrogen contents in the input gas particularly high yields of methanol in the pre-reactor are achieved, thus resulting in further savings in respect of the input gas compressor. It has especially been found that the inventive carbon dioxide contents result in particularly rapid establishment of thermodynamic equilibrium of the methanol synthesis reaction and are thus kinetically favored. Synthesis gases produced on the basis of SMR or a combination of autothermal reforming and SMR regularly have $CO_2$ contents of markedly above 5% by volume and are therefore less preferred.

A preferred embodiment of the process according to the invention is characterized in that the input gas has a stoichiometry number SN of 1.5 to 3.0 before introduction into the pre-reactor stage, wherein $$SN = \frac{n(H_2) - n(CO_2)}{n(CO) + n(CO_2)}, \text{ where } n \text{ is in [mol]}$$

The stoichiometry number indicates the stoichiometric ratios of the methanol synthesis reaction At ideal stoichiometric ratios and in the absence of carbon dioxide the stoichiometry number is 2 However, studies have shown that smaller carbon dioxide amounts can increase the CO conversion in the pre-reactor so that the stoichiometry number is preferably in a range from 1.8 to 3.0. Preferably 1.8≤SN≤2.5, particularly preferably 1.9≤SN≤2.2 and more preferably 1.95≤SN≤2.05.

A preferred embodiment of the process according to the invention is characterized in that the input gas has a pressure of 20 to 100 bar, preferably a pressure of 35 to 55 bar.

Studies have shown that in the inventive pressure range in combination with the inventive carbon monoxide contents, optionally hydrogen contents and optionally carbon dioxide contents in the input gas particularly high yields of methanol in the pre-reactor are achieved, thus resulting in further savings in respect of the input gas compressor.

A preferred embodiment of the process according to the invention is characterized in that the input gas produced and present under elevated pressure is introduced into the pre-reactor stage without further pressurization. In particular the input gas produced and present under elevated pressure is introduced into the pre-reactor stage without further pressurization by a gas compressor.

The input gas comprising hydrogen and carbon monoxide is typically produced at elevated pressure, for example in the context of a coal gasification, and may be introduced into the pre-reactor without further compression by a gas compressor for example. This reduces the total number of required compressors, for example to one gas compressor for compressing the residual gas from the pre-reactor stage and one gas compressor for compressing the recycle gas when using a synthesis circuit.

A preferred embodiment of the process according to the invention is characterized in that the residual gas of the residual gas stream is compressed to a pressure higher than that of the input gas before introduction into the main reactor stage. The residual gas stream is preferably compressed to a higher pressure before introduction into the main reactor stage by a gas compressor.

Even in the so-called low-pressure processes for producing methanol the main reactor stage requires pressures of 60 bar to 120 bar and the residual gas of the residual gas stream must be compressed to said pressures before introduction into the main reactor stage. The pressure in the main reactor stage is regularly higher than the pressure of the input gas produced at and under elevated pressure.

Before introduction into the main reactor stage the residual gas stream is compressed at least to a pressure at least 5 bar higher than the pressure of the input gas, or to a pressure at least 10 bar higher, or to a pressure at least 25 bar higher or to a pressure at least 40 bar higher.

A preferred embodiment of the process according to the invention is characterized in that the main reactor stage is part of a synthesis circuit, wherein a recycle gas stream remaining after separation of the methanol from the second methanol-containing product stream is recycled to the main reactor stage in the synthesis circuit and combined with the residual gas stream. The recycle gas of the recycle gas stream is also compressed to a pressure higher than that of the input gas before or where the recycle gas is combined with the residual gas. The compression is likewise accomplished using a gas compressor, in this case referred to as a recycle gas compressor. As an alternative the use of a single, especially multistage, gas compressor which compresses the residual gas stream and the recycle gas stream to the reaction pressure required for the methanol synthesis in the main reactor stage is conceivable. After compression to reaction pressure the recycle gas and the residual gas are converted into a second methanol-containing product stream in the main reactor stage as a combined gas stream.

A preferred embodiment of the process according to the invention comprising the synthesis circuit is characterized in that for a recirculation rate R defined as $$R = \frac{\text{volume flow (recycle gas stream)}}{\text{volume flow (residual gas stream)}},$$

$$R \leq 2.5.$$

It is preferable when $1.5 \leq R \leq 2.5$ and particularly preferable when $1.5 \leq R \leq 2$.

A preferred embodiment of the process according to the invention is characterized in that the main reactor stage comprises a number n of serially arranged partial reactor stages and the second methanol-containing product stream n comprises methanol-containing partial product streams, wherein methanol is separated from the n methanol-containing partial product streams and discharged from the main reactor stage.

Alternatively to the configuration of the main reactor stage as a synthesis circuit the configuration of the main reactor stage as a system of serially arranged partial reactor stages is conceivable. A partial reactor stage preferably corresponds to a reactor into which an nth partial residual gas stream is introduced, wherein the partial reactor stage is traversed by the nth partial residual gas stream once in a single pass and an nth methanol-containing partial product stream is discharged from each partial reactor stage.

A preferred embodiment of the process according to the invention is characterized in that the pre-reactor stage comprises a water-cooled reactor.

The cooling of the reactor of the pre-reactor stage is preferably carried out via water boiling under elevated pressure, wherein the thus produced steam is sent to a steam drum for energy recovery.

A preferred embodiment of the process according to the invention is characterized in that the water-cooled reactor has a cooling temperature of 180° C. to 250° C. The water-cooled reactor preferably has a cooling temperature of less than 235° C., especially and preferably a cooling temperature of 200° C. to 235° C.

The cooling temperature is to be understood as meaning the temperature of the medium used for cooling at the outlet of the cooled side of the reactor. On the process side the temperature along the catalyst bed adapts to the selected cooling temperature. It is essential that said temperature does not fall below a certain temperature in order to ensure operation above the ignition temperature of the catalyst.

A preferred embodiment of the process according to the invention is characterized in that the main reactor stage comprises a water-cooled reactor. The main reactor stage preferably additionally comprises a gas-cooled reactor, wherein the gas-cooled reactor is especially arranged downstream of the water-cooled reactor.

As studies have shown the use of a combination of water-cooled and gas-cooled reactors results in particularly large savings in respect of compressor output. Expenditure in respect of the altogether required catalyst volume is slightly higher due to the use of two reactors though this is compensated by the additionally saved compressor output.

An alternative embodiment thereto is characterized in that the main reactor stage does not comprise a gas-cooled reactor. The main reactor stage especially comprises solely a water-cooled reactor.

As studies have shown the savings in respect of compressor output when using a single water-cooled reactor are only immaterially lower compared to a configuration comprising a water-cooled reactor and a gas-cooled reactor. However, the slightly higher compressor output required is compensated by the fact that the total catalyst volume may be reduced.

If both the pre-reactor stage and the main reactor stage each comprise a water-cooled reactor, both water-cooled stages may be operated with the same cooling system. In other words the pre-reactor stage and the main reactor stage are fed by a common cooling system. It is preferable when both stages have the same target cooling temperature.

The abovementioned configurations are employed especially when the main reactor stage is configured as a synthesis circuit. The synthesis circuit then preferably comprises either a water-cooled reactor and a downstream gas-cooled reactor or alternatively solely a water-cooled reactor The objects of the invention are further at least partially achieved by a plant for producing methanol from an input gas comprising carbon monoxide (CO) and hydrogen ($H_2$) comprising a feed conduit for introducing input gas under elevated pressure into a pre-reactor stage, wherein the pre-reactor stage is configured for catalytic conversion of the input gas into a first methanol-containing product stream;

a first separator arranged downstream of the pre-reactor stage and connected via a conduit to the pre-reactor stage for separation of methanol from the first methanal-containing product stream and for separation of a residual gas stream;

a feed conduit connected to the first separator for introducing the residual gas stream into a gas compressor;

a feed conduit for introducing the residual gas stream compressed to reaction pressure in the gas compressor into a main reactor stage, wherein the main reactor stage is configured for catalytic conversion of the residual gas stream into a second methanol-containing product stream;

a second separator arranged downstream of the main reactor stage and connected via a conduit to the main reactor stage for separation of methanol from the second methanol-containing product stream, characterized in that the pre-reactor stage is configured for conversion of an input gas having a carbon monoxide content of 25% to 36% by volume.

The objects of the invention are further at least partially achieved by the use of an abovementioned plant for producing methanol from an input gas comprising carbon monoxide (CO) and hydrogen ($H_2$) for converting an input gas having a carbon monoxide content of 25% to 36% by volume.

It is preferable when the input gas has been produced by gasification of coal, by autothermal reforming or gas POX.

BRIEF DESCRIPTION OF THE FIGURES

The invention is more particularly elucidated hereinbelow by way of examples without in any way limiting the subject-matter of the invention. Further features, advantages and possible applications of the invention will be apparent from the following description of the working examples in connection with the drawings and the numerical examples.

In the figures

DETAILED DESCRIPTION OF THE PREFERRED EMBODIMENTS

Input Gas

The input gas is a gas mixture comprising at least carbon monoxide (CO) and hydrogen ($H_2$) as gas components. This makes the input gas suitable for producing methanol. Depending on the type of production the input gas is especially a synthesis gas, water gas or cracking gas. The input gas is preferably but without limitation produced by gasification of coal. Pure autothermal reformers (ATR) or plants for the partial oxidation of gaseous carbon-containing inputs (gas PDX) may also produce synthesis gases having a high CO content which are suitable for the process according to the invention.

Also suitable as a carbon monoxide source is an electrolysis of carbon dioxide which preferably produces a CO-rich material stream using electricity from renewable energy sources, In one embodiment of the invention the input gas has a carbon monoxide content of 25% to 36% by volume, This reported content and further reported contents mentioned in the context of the invention always relate to the dry input gas. Dry input gas is to be understood as meaning that water has been completely or substantially completely removed from the input gas. In one example water was removed to a residual content of not more than 1% by volume or not more than 0.5% by volume or not more than 0.3% by volume or not more than 0.1% by volume.

The input gas typically comprises carbon dioxide ($CO_2$) as a further component. In certain cases carbon dioxide is removed completely or at least down to trace levels in the context of gas scrubbing, for example gas scrubbing with methanol as the scrubbing medium.

Optional components in the input gas are for example methane ($CH_4$) and inert constituents such as nitrogen ($N_2$) or argon (Ar).

The input gas, in particular input gas from a coal gasification, is typically subjected, prior to its use, to a gas scrub for removal of sulfur-containing components such as hydrogen sulfide ($H_2S$) and carbonyl sulfide (COS) since sulfur-containing substances are poisons for the catalysts used in the methanol synthesis. Carbon dioxide is typically also removed to a certain extent in the context of gas scrubbing but in most cases the carbon dioxide removal is incomplete. The gas scrub may be a process operating according to the principle of physical absorption or chemical absorption for example. One example of a gas scrubbing process operating according to the principle of physical absorption is methanol scrubbing, also known as the Rectisol process. One example of a gas scrubbing process operating according to the principle of chemical absorption is gas scrubbing using amines.

In order to establish a certain ratio of carbon monoxide to hydrogen and/or to establish a certain proportion of carbon dioxide in the input gas the input gas may partly contain synthesis gas from a water gas shift reaction. The water gas shift reaction is used to increase the hydrogen proportion while simultaneously reducing the carbon monoxide proportion in a synthesis gas, water gas or cracking gas. Since the input gas shall preferably have a high carbon monoxide content the proportion in the input gas of a gas that has been subjected to a water gas shift reaction is preferably low.

The input gas is produced under elevated pressure and is under elevated pressure before introduction into the pre-reactor stage. Production of the input gas is typically carried out at a pressure markedly above atmospheric pressure, regularly at least 20 bar and up to 100 bar. The pressure at which the input gas is produced corresponds substantially to the pressure that the input gas is under before introduction into the pre-reactor stage. As a result of unavoidable pressure drops the pressure at introduction into the pre-reactor is slightly lower than during production.

Pre-Reactor Stage, Main Reactor Stage, Residual Gas Stream

The input gas is initially supplied to the pre-reactor stage. Said stage performs a partial conversion of the input gas into a first methanol-containing product stream which contains not only methanol but, depending on the carbon dioxide content of the input gas, also water. The first methanol-containing product stream (and also further methanol-containing product streams) further comprises byproducts such as for example dimethyl ether, methyl formate, acetone, ethanol and higher alcohols. The mixture of the methanol-containing product stream is preferably discharged from the pre-reactor stage after condensation in a separator. Remaining input gas not converted in the pre-reactor stage—also referred to as residual gas—is supplied to the main reactor stage as a residual gas stream. The main reactor stage performs the largely complete conversion of the residual gas into a (second) methanol-containing product stream in turn comprising methanol, water and byproducts. The second methanol-containing product stream is in turn discharged from the main reactor stage preferably after condensation in a separator.

The pressure in the main reactor stage is generally higher than the pressure in the pre-reactor stage and a gas compressor—also referred to here as a residual gas compressor—is therefore necessary to compress the residual gas to the pressure required in the main reactor stage.

Methanol-containing product streams from the pre-reactor stage and the main reactor stage are typically combined and worked up to produce methanol with a pre-determined purity.

Reaction Pressure

The reaction pressure is the pressure prevailing and required for the catalytic conversion of the constituents of the residual gas and/or recycle gas into methanol at which the residual gas and/or the recycle gas are introduced into the main reactor stage.

In one example the reaction pressure in the relevant reactor is 60 to 120 bar, preferably 70 to 100 bar, particularly preferably 75 to 90 bar and more preferably 75 to 85 bar.

Synthesis Circuit and Recycle Gas Stream

If the main reactor stage is configured as a synthesis circuit the reactor or the (serially arranged) reactors of the main reactor stage are supplied with a portion of residual gas as a residual gas stream from the pre-reactor stage and a portion of recycle gas which has already traversed the reactor or the reactors of the main reactor stage. In one example both the residual gas stream and the recycle gas stream are each compressed by a dedicated gas compressor to the pressure of the main reactor stage required for the methanol synthesis reaction. In a further example a single gas compressor comprising a plurality of compression stages is used for compression of both gas streams. In this case the recycle gas stream may be supplied directly to the second compression stage together with the residual gas stream, wherein both gas streams are compressed to reaction pressure.

The ratio of the volume flow of the recycle gas stream to the volume flow of the residual gas stream is referred to as the recirculation rate R.

Partial Reactor Stage

If the pre-reactor stage or the main reactor stage each comprises a plurality of reactors each of the reactors may also be referred to as a partial reactor stage (of the pre-reactor stage or the main reactor stage).

Figure 1:
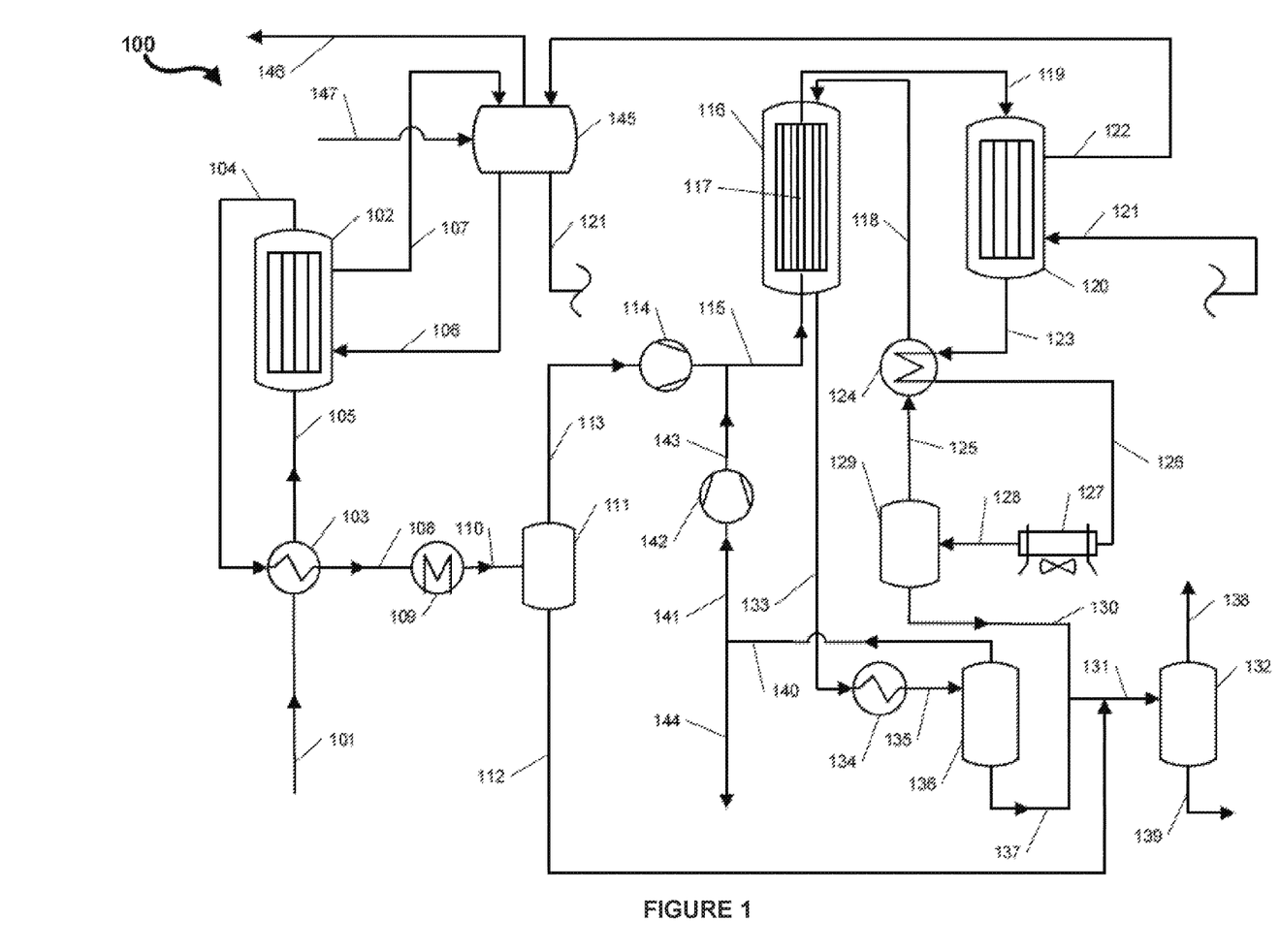
FIG. 1 is a schematic flow diagram representation of an inventive process 100 or an inventive plant 100 according to a first example of the invention and FIG. 2 is a schematic flow diagram representation of an inventive process 200 or an inventive plant 200 according to a second example of the invention.

In the example according to FIG. 1, the process according to the invention comprises a main reactor stage configured as a synthesis circuit. The synthesis circuit comprises a water-cooled reactor (WCR) and a gas-cooled reactor (GCR) as partial reactor stages. Synthesis gas from a coal gasification plant is supplied via conduit 101 to the pre-reactor 102 at a pressure of 50 bar. The pre-reactor stage according to FIG. 1 comprises only the pre-reactor 102. Synthesis gas in conduit 101 has a CO content of 29.3% by volume, an $H_2$ content of 67.8% by volume, a $CO_2$ content of 2.53% by volume and as residual constituents methane ($CH_4$) and inert constituents such as for example nitrogen ($N_2$).

Synthesis gas from conduit 101 is preheated in heat exchanger 103 against methanol-containing product stream from conduit 104 and introduced into pre-reactor 102 via conduit 105. Pre-reactor 102 is configured as a water-cooled reactor and is cooled by boiling water under elevated pressure. The water is supplied from steam drum 145 via conduit 106 and at least partially evaporated on the cooling side of the reactor. Steam drum 145 is fed with boiler feed water 147, The steam or a partially evaporated stream exits the cooling side of the reactor via conduit 107 and is supplied to steam drum 145. The produced steam is discharged from steam drum 145 as export steam 146 and may be used for example as heating steam at another location.

In pre-reactor 102 CO, $H_2$ and $CO_2$ are partially converted into methanol over a copper-based fixed bed catalyst at a cooling temperature of about 230° C. Resulting first methanol-containing product stream in conduit 104 is pre-cooled against synthesis gas from conduit 101 in heat exchanger 103 and supplied via conduit 108 to product cooler 109. Cooled methanol-containing product subsequently passes via conduit 110 into separator 111 in which a separation of the methanol-containing product stream into a liquid phase and a gaseous phase is carried out. Condensed crude methanol is withdrawn from separator 111 via conduit 112 and combined with crude methanol from conduit 131.

Unconverted synthesis gas is discharged from separator 111 as a residual gas stream via conduit 113 and supplied to a compressor (residual gas compressor) 114 in which the residual gas is compressed to a pressure of 80 bar before it is introduced as a residual gas stream via conduit 115 together with the recycle gas stream from conduit 143 into the main reactor stage which comprises a gas-cooled reactor and a water-cooled reactor.

In the main reactor stage residual gas stream and recycle gas stream from conduit 115 are initially passed through a multiplicity of internal tubes 117 of the gas-cooled reactor 116 in which residual gas and recycle gas from conduit 115 are preheated while reacting residual gas and recycle gas from conduit 118 are cooled on the outside of the internal tubes. Preheated residual gas and recycle gas pass via conduit 119 into water-cooled reactor 120 where they are partially converted into methanol over a copper-based fixed bed catalyst at a cooling temperature of about 230° C. Water-cooled reactor 120 is cooled by boiling water under elevated pressure. The water is supplied from steam drum 145 via conduit 121. Steam or a partially evaporated stream exits the cooling side of the reactor via conduit 122 and is supplied to steam drum 145. The produced steam is discharged from steam drum 145 as export steam 146 and may be used for example as heating steam at another location.

The reaction of the residual gas and the recycle gas in the water-cooled reactor 120 affords a second methanol-containing (partial) product stream which is discharged from water-cooled reactor 120 via conduit 123 and pre-cooled against residual gas/recycle gas from conduit 125 in heat exchanger 124. The pre-cooled methanol-containing product stream subsequently passes via conduit 126 into air cooler 127 and via conduit 128 into high-pressure separator 129 in which a separation of the methanol-containing product stream into a liquid phase and a gaseous phase is carried out. Condensed crude methanol is withdrawn from high-pressure separator 129 via conduit 130 and further supplied via conduit 131 to low-pressure separator 132. The gas phase separated in the high-pressure separator is withdrawn as a residual gas and recycle gas stream via conduit 125 and heated against the methanol-containing product stream from conduit 123 in heat exchanger 124 and introduced into the gas-cooled reactor 116 via conduit 118. In the gas-cooled reactor 116 a partial conversion of the residual gas/recycle gas from conduit 118 into a second methanol-containing product is carried out on the outside of the internal tubes 117 over a copper-based fixed bed catalyst and said product is withdrawn via conduit 133 as a second methanol-containing (partial) product stream. Methanol-containing product is subsequently cooled in product cooler 134 and supplied via conduit 135 into high-pressure separator 136. Crude methanol withdrawn from high-pressure separator 136 via conduit 137 is combined with crude methanol from conduit 130 and conduit 112 in conduit 131. Further gas constituents dissolved in crude methanol are separated from the mixed crude methanol in low-pressure separator 132 and exit the low-pressure separator 132 via conduit 138. The gases withdrawn from the low-pressure separator via conduit 138 comprise about 30% by volume of hydrogen and about 25% by volume of methane and may be utilized for example for combustion in a burner for steam reforming. Condensed crude methanol is withdrawn from the low-pressure separator 132 via conduit 139 and sent for further workup to obtain pure methanol.

Gas separated in high-pressure separator 136 is withdrawn from high-pressure separator 136 via conduit 140 as a recycle gas stream and via conduit 141 supplied to a compressor (recycle gas compressor) 142 in which the recycle gas is compressed to a pressure of 80 bar. The recycle gas stream is combined with the residual gas stream in conduit 115 via conduit 143 and again as a combined stream of residual gas and recycle gas supplied first to the water-cooled reactor 120 and then to the gas-cooled reactor 116.

The ratio of the recycle gas stream to the residual gas stream, also known as the recirculation rate R, is 1.9 in the example of FIG. 1. A purge gas is diverted from the recycle gas in conduit 140 via conduit 144 and contains not only constituents that are inert per se such as nitrogen and constituents that are inert in respect of the methanol synthesis such as methane but also for example unconverted hydrogen which may subsequently be recovered for example using a pressure swing absorption apparatus (not shown).

Figure 2:
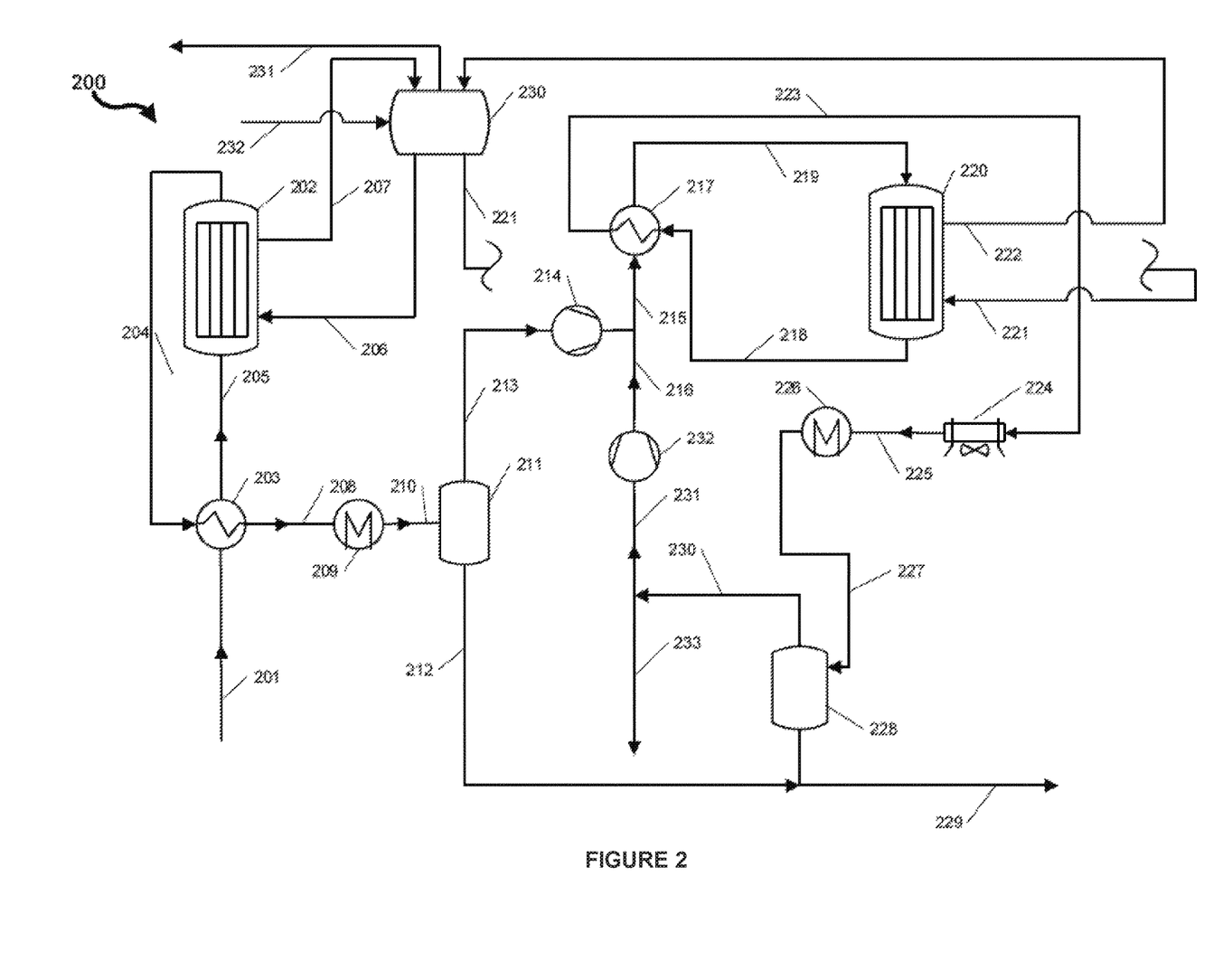

In the example according to FIG. 2, the process according to the invention likewise comprises a main reactor stage configured as a synthesis circuit. The synthesis circuit comprises only a water-cooled reactor (WCR) as a reactor stage and no gas-cooled reactor (GCR). Synthesis gas from a coal gasification plant is supplied via conduit 201 to pre-reactor 202 at a pressure of 50 bar. The pre-reactor stage according to FIG. 2 comprises only the pre-reactor 202. Synthesis gas in conduit 201 has a CO content of 29.3% by volume, an $H_2$ content of 67.8% by volume, a $CO_2$ content of 2.53% by volume and as residual constituents methane ($CH_4$) and inert constituents such as for example nitrogen.

Synthesis gas from conduit 201 is preheated in heat exchanger 203 against methanol-containing product stream from conduit 204 and introduced into pre-reactor 202 via conduit 205. Pre-reactor 202 is configured as a water-cooled reactor and is cooled by boiling water under elevated pressure. The water is supplied from steam drum 230 via conduit 206 and at least partially evaporated on the cooling side of the reactor. Steam or a partially evaporated stream exits the cooling side of the reactor via conduit 207 and is supplied to steam drum 230. The produced steam is discharged from steam drum 230 as export steam 231 and may be used for example as heating steam at another location.

In pre-reactor 202 CO, $H_2$ and $CO_2$ are partially converted into methanol over a copper-based fixed bed catalyst at a cooling temperature of about 230° C. Resulting first methanol-containing product stream in conduit 204 is pre-cooled against synthesis gas from conduit 201 in heat exchanger 203 and supplied via conduit 208 to product cooler 209. Cooled methanol-containing product subsequently passes via conduit 210 into separator 211 in which a separation of the methanol-containing product stream into a liquid phase and a gaseous phase is carried out. Liquid crude methanol is withdrawn from separator 211 via conduit 212 and combined with crude methanol from conduit 229.

Unconverted synthesis gas is discharged from separator 211 as a residual gas stream via conduit 213 and supplied to a compressor (residual gas compressor) 214 in which the residual gas is compressed to a pressure of 80 bar before it is introduced as a residual gas stream via conduit 215 together with the recycle gas stream from conduit 216 into the main reactor stage which comprises solely a water-cooled reactor.

In the main reactor stage residual gas stream and recycle gas stream from conduit 215 are initially preheated in heat exchanger 217 against second methanol-containing product stream from conduit 218 and then introduced via conduit 219 into the water cooled reactor 220. In water-cooled reactor 220 residual gas/recycle gas are partially converted into methanol over a copper-based fixed bed catalyst at a cooling temperature of about 230° C. Water-cooled reactor 220 is cooled by boiling water under elevated pressure which is supplied via conduit 221. Steam or a partially evaporated stream exits the cooling side of the reactor via conduit 222 and is supplied to steam drum 230. The steam produced in steam drum 230 is discharged from steam drum 230 as export steam 231 and may be used for example as heating steam at another location. The reaction of the residual gas and the recycle gas in the water-cooled reactor 220 affords a second methanol-containing (partial) product stream which is discharged from water-cooled reactor 220 via conduit 218 and pre-cooled against residual gas/recycle gas from conduit 215 in heat exchanger 217. The pre-cooled methanol-containing product stream subsequently passes via conduit 223 into air cooler 224, via conduit 225 into product cooler 226 and finally via conduit 227 into separator 228 in which a separation of the methanol-containing product stream into a liquid phase and a gaseous phase is carried out. Crude methanol is withdrawn from separator 228 via conduit 229 and together with crude methanol from conduit 212 for example may be subjected to further workup to afford pure methanol.

Gas separated in separator 228 is withdrawn from separator 228 via conduit 230 as a recycle gas stream and via conduit 231 supplied to a compressor (recycle gas compressor) 232 in which the recycle gas is compressed to a pressure of 80 bar. The recycle gas stream is combined with the residual gas stream in conduit 215 via conduit 216 and as a combined stream of residual gas and recycle gas supplied to the water-cooled reactor 220.

The ratio of the recycle gas stream to the residual gas stream, also known as the recirculation rate R, is 2.4 in the example of FIG. 2. A purge gas is diverted from the recycle gas in conduit 230 via conduit 233 and contains not only constituents that are inert per se such as nitrogen but also constituents that are inert in the methanol synthesis such as methane and for example unconverted hydrogen which may subsequently be recovered for example using a pressure swing absorption apparatus (not shown).

EXAMPLES

The following numerical examples are intended to further elucidate the technical effect of the present invention.

The following table comprising three comparative examples (noninventive) examines the effect of the pre-reactor on achievable savings in respect of total compressor output (output of the residual gas compressor and of the recycle gas compressor) for a synthesis gas from combined reforming. The synthesis gas has a relatively low carbon monoxide content of 20.9% by volume and a relatively high carbon dioxide content of 8.46% by volume. The required compressor output of 31.5 MW according to Comparative Example 1 (without pre-reactor) was normalized to 100%. In the case of Comparative Example 2 (with pre-reactor, configuration as per representation in FIG. 1) a saving of 5% was achieved. In the case of Comparative Example 3 (with pre-reactor, configuration as per representation in FIG. 2) a saving of 19.5% was achieved. Savings of less than 10% of total compressor output do not justify the use of a pre-reactor. Although the saving is higher in the comparative example it is nevertheless significantly lower than in the analogous Example 2 in which the required total catalyst volume is also significantly lower,

| Setup | Comparative Exampl 1 (without pre-reactor) (WCR + GCR) No reactor at low process pressure; two reactors at high process pressure | Comparative Example 2 (with pre-reactor) (WCR + GCR) 1 reactor at low process pressure; two reactors at high process pressure | Comparative Example 3 (with pre-reactor) (only WCR) 1 reactor at low process pressure; 1 reactor at high process pressure |
|---|---|---|---|
| CO content/ % by vol. | 20.9 | 20.9 | 20.9 |
| $H_2$ content/ % by vol. | 68.7 | 68.7 | 68.7 |
| $CO_2$ content/ % by vol. | 8.46 | 8.46 | 8.46 |
| $CH_4 + N_2$ | trace | trace | trace |
| Pressure in pre-reactor/ bar | 30 | 30 | 30 |
| Pressure in WCR/bar | 76 | 76 | 7 |

| Setup | Comparative Exampl 1 (without pre-reactor) (WCR + GCR) No reactor at low process pressure; two reactors at high process pressure | Comparative Example 2 (with pre-reactor) (WCR + GCR) 1 reactor at low process pressure; two reactors at high process pressure | Comparative Example 3 (with pre-reactor) (only WCR) 1 reactor at low process pressure; 1 reactor at high process pressure |
|---|---|---|---|
| Pressure in GCR/bar | 74 | 74 | n/a |
| Methanol production/tons/d | 5053.1 | 5053.1 | 5053.1 |
| Total compressor output/MW | 31.5 | 29.9 | 25.4 |
| Recirculation rate | 2.1 | 2.2 | 4.1 |
| Catalyst volume/m³ | 335.2 | 352.6 | 319.7 |
| Total space-time yield/kg/l/h | 0.6 | 0.6 | 0.7 |
| Normalized total compressor output/% | 100.0 | 95.0 | 80.5 |
| Normalized catalyst volume/% | 100.0 | 105.2 | 95.4 |

The following table comprising a fourth Comparative Example (noninventive) and two Inventive Examples examines the effect of the pre-reactor on achievable savings in respect of compressor output for a synthesis gas from coal gasification. Compared to the case in the above table the synthesis gas has a markedly higher carbon monoxide content of 29.3% by volume and a markedly lower carbon dioxide content of 2.53% by volume. The required compressor output of 17.1 MW according to Comparative Example 4 (without pre-reactor) was normalized to 100%. Example 1 corresponds to the configuration according to FIG. 1 and the accompanying description. Example 2 corresponds to the configuration according to FIG. 2 and the accompanying description. Compared to Comparative Example 4 (without pre-reactor), Example 1 achieved a surprisingly high percentage saving in respect of compressor output of 31.7%. Compared to Comparative Example 4 (without pre-reactor), Example 2 achieved a surprisingly high percentage saving in respect of compressor output of 27.9%. There is therefore a synergistic effect on achievable savings in respect of compressor output when pursuing a pre-reactor concept in conjunction with input gases having a high CO content. In other words input gases having high carbon monoxide contents according to the invention justify the use of a pre-reactor on account of significant savings in respect of the total compressor output required.

Simultaneously, according to Example 2 the required total catalyst volume at unchanged production amount is reduced significantly by 17.4% and the space-time yield is improved in advantageous fashion.

| Setup | Comparatiave Example 4 without pre-reactor (WCR + GCR) No reactor at low process pressure; two reactors at high process pressure | Example 1 (with pre-reactor) (WCR + GCR) 1 reactor at low process pressure; two reactors at high process pressure | Example 2 (with pre-reactor) (only WCR) 1 reactor at low process pressure; 1 reactor at high process pressure |
|---|---|---|---|
| CO content/% by vol. | 29.3 | 29.3 | 29.3 |
| H₂ content/% by vol. | 67.8 | 67.8 | 67.8 |
| CO₂ content/% by vol. | 2.53 | 2.53 | 2,53 |
| CH₄ + N₂ | trace | trace | trace |
| Pressure in pre-reactor/bar | 50 | 50 | 50 |
| Pressure in WCR/bar | 80 | 80 | 80 |
| Pressure in GCR/bar | 78 | 78 | n/a |
| Methanol production/tons/d | 5440.5 | 5440.5 | 5440.5 |
| Total compressor output/MW | 17.1 | 11.7 | 12.3 |
| Recirculation rate | 1.6 | 1.9 | 2.4 |
| Catalyst volume/m³ | 176.8 | 186.9 | 146.0 |
| Total space-time yield/kg/l/h | 1.3 | 1.2 | 1.6 |
| Normalized total compressor output/% | 100.0 | 68.3 | 72.1 |
| Normalized catalyst volume/% | 100.0 | 105.7 | 82.6 |

Embodiments of the invention are described with reference to different types of subject-matter. In particular, certain embodiments are described with reference to process claims while other embodiments are described with reference to apparatus claims. However, it will be apparent to a person skilled in the art from the description hereinabove and hereinbelow that unless otherwise stated in addition to any combination of features belonging to one type of claim any combination of features relating to different types of subject-matter or types of claim may also be contemplated. All features may be combined to achieve synergistic effects which go beyond simple summation of the technical features.

While the invention has been represented and described in detail in the drawing and the preceding description, such a representation and description shall be considered to be illustrative or exemplary and non-limiting. The invention is not limited to the disclosed embodiments. Other variations of the disclosed embodiments may be understood and executed by those skilled in the art of the field of the claimed invention from a study of the drawing, the disclosure and the dependent claims.

In the claims, the word "having" or "comprising" does not exclude further elements or steps and the indefinite article "a" or "an" does not exclude a plurality. Reference numerals in the claims should not be interpreted as limiting the scope of the claims.

LIST OF REFERENCE NUMERALS

- 100 Process or plant
- 101 Conduit
- 102 Pre-reactor
- 103 Heat exchanger
- 104-108 Conduit
- 109 Product cooler
- 110 Conduit
- 111 Separator
- 112, 113 Conduit
- 114 Compressor
- 115 Conduit
- 116 Gas-cooled reactor (GCR)
- 117 Internal tubes
- 118, 119 Conduit
- 120 Water-cooled reactor (WCR)
- 121-123 Conduit
- 124 Heat exchanger
- 125, 126 Conduit
- 127 Air cooler
- 128 Conduit
- 129 High-pressure separator
- 130, 131 Conduit
- 132 Low-pressure separator
- 133 Conduit
- 134 Product cooler
- 135 Conduit
- 136 High-pressure separator
- 137-141 Conduit
- 142 Compressor
- 143, 144 Conduit
- 145 Steam drum
- 146 Export steam
- 147 Boiler feed water
- 200 Process or plant
- 201 Conduit
- 202 Pre-reactor
- 203 Heat exchanger
- 204-208 Conduit
- 209 Product cooler
- 210 Conduit
- 211 Separator
- 212, 213 Conduit
- 214 Compressor
- 215, 216 Conduit
- 217 Heat exchanger
- 218, 219 Conduit
- 220 Water-cooled reactor
- 221-223 Conduit
- 224 Air cooler
- 225 Conduit
- 226 Product cooler
- 227 Conduit
- 228 Separator
- 229 Conduit
- 230 Steam drum
- 231 Export steam
- 232 Boiler feed water

What is claimed is:

1. A process for producing methanol from an input gas comprising carbon monoxide and hydrogen, the process comprising:
   introducing an input gas produced at and under elevated pressure into a pre-reactor stage as an input gas stream for catalytic conversion into a first methanol-containing product stream,
   separating methanol from the first methanol-containing product stream and discharging the separated methanol from the pre-reactor stage,
   compressing a residual gas of the remaining input gas stream to a reaction pressure as a residual gas stream and introducing the compressed residual gas into a main reactor stage for catalytic conversion into a second methanol-containing product stream, and
   separating methanol from the second methanol-containing product stream and discharging the separated methanol from the main reactor stage,
   wherein the input gas has a carbon monoxide content of 25% to 36% by volume before introduction into the pre-reactor stage,
   wherein the residual gas is compressed between 5 bar and 40 bar.

2. The process according to claim 1, wherein the input gas has a hydrogen content of 66% to 72% by volume before introduction into the pre-reactor stage.

3. The process according to claim 1, wherein the input gas has a carbon dioxide content of not more than 5% by volume before introduction into the pre-reactor stage.

4. The process according to claim 1, wherein the input gas has a stoichiometry number SN of 1.5 to 3.0 before introduction into the pre-reactor stage, wherein $$SN = \frac{n(H_2) - n(CO_2)}{n(CO) + n(CO_2)}, \text{ where } n \text{ is in [mol]}.$$

5. The process according to claim 1, wherein the input gas has a pressure of 20 to 100 bar.

6. The process according to claim 1, wherein the input gas produced and present under elevated pressure is introduced into the pre-reactor stage without further pressurization.

7. The process according to claim 1, wherein the residual gas of the residual gas stream is compressed to a pressure higher than that of the input gas before introduction into the main reactor stage.

8. The process according to claim 1, wherein the main reactor stage is part of a synthesis circuit, wherein a recycle gas stream remaining after separation of the methanol from the second methanol-containing product stream is recycled to the main reactor stage in the synthesis circuit and combined with the residual gas stream.

9. The process according to claim 8, wherein for a recirculation rate R defined as $$R = \frac{\text{volume flow (recycle gas stream)}}{\text{volume flow (residual gas stream)}},$$

$R \leq 2.5$.

10. The process according to claim 1, wherein the main reactor stage comprises a number n of serially arranged partial reactor stages and the second methanol-containing product stream n comprises methanol-containing partial product streams, wherein methanol is separated from the n methanol-containing partial product streams and discharged from the main reactor stage.

11. The process according to claim 1, wherein the pre-reactor stage comprises a water-cooled reactor.

12. The process according to claim 11, wherein the water-cooled reactor has a cooling temperature of 180° C. to 250° C.

13. The process according to claim 1, wherein the main reactor stage comprises a water-cooled reactor.

14. The process according to claim 13, wherein the main reactor stage additionally comprises a gas-cooled reactor.

15. The process according to claim 13, wherein the main reactor stage does not comprise a gas-cooled reactor.

* * * * *